United States Patent
Kahlman et al.

(10) Patent No.: US 10,687,729 B2
(45) Date of Patent: Jun. 23, 2020

(54) APPARATUS AND METHOD FOR ESTIMATING A VALUE OF A PHYSIOLOGICAL CHARACTERISTIC

(71) Applicant: KONINKLIJKE PHILIPS N.V., Eindhoven (NL)

(72) Inventors: Josephus Arnoldus Henricus Maria Kahlman, Tilburg (NL); Rick Bezemer, Amsterdam Zuidoost (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1005 days.

(21) Appl. No.: 14/935,727

(22) Filed: Nov. 9, 2015

(65) Prior Publication Data
US 2016/0143557 A1  May 26, 2016

(30) Foreign Application Priority Data
Nov. 24, 2014  (EP) .................................... 14194503

(51) Int. Cl.
*A61B 5/05* (2006.01)
*A61B 5/00* (2006.01)
(Continued)

(52) U.S. Cl.
CPC .............. *A61B 5/05* (2013.01); *A61B 5/6898* (2013.01); *A61B 5/7228* (2013.01);
(Continued)

(58) Field of Classification Search
CPC .................................................. A61B 5/0265
See application file for complete search history.

(56) References Cited

U.S. PATENT DOCUMENTS 5,688,050 A * 11/1997 Sterzer ................... A61B 5/015
  374/121
6,359,597 B2 * 3/2002 Haj-Yousef .............. G01V 3/12
  128/204.23
(Continued)

FOREIGN PATENT DOCUMENTS

EP   2417908 A1   2/2012
EP   1647306 B1   3/2012
(Continued)

OTHER PUBLICATIONS

Adib et al, "Multi-Person Motion Tracking via RF Body Reflections", Computer Science and Artificial Intelligence Laboratory Technical Report, MIT-CSAIL-TR-2014-008, 2014, p. 1-14.
(Continued)

*Primary Examiner* — Luther Behringer

(57) ABSTRACT

There is provided a measurement apparatus for estimating a value of a physiological characteristic of a subject. The apparatus comprises a radio-frequency (RF) power generating apparatus, a detector, and a controller in communication with the RF power generating apparatus. The RF power generating apparatus comprises a transmit antenna for emitting RF radiation; an RF signal generator; and a transmission line connecting the RF signal generator to the transmit antenna. The detector is arranged to measure the variation of at least one parameter correlated with attenuation of the emitted RF radiation, during the measurement period. The controller is arranged to: cause the RF power generating apparatus to emit RF radiation during a measurement period; receive measurements of the variation of the at least one parameter from the detector; and calculate a value of a physiological characteristic of a subject based on the received measurements.

19 Claims, 4 Drawing Sheets

(51) Int. Cl.
*A61B 90/98* (2016.01)
*A61B 5/0265* (2006.01)
*A61B 5/053* (2006.01)
*A61B 5/024* (2006.01)

(52) U.S. Cl.
CPC ............ *A61B 5/7278* (2013.01); *A61B 90/98* (2016.02); *A61B 5/0265* (2013.01); *A61B 5/02438* (2013.01); *A61B 5/0535* (2013.01); *A61B 5/7246* (2013.01)

(56) References Cited

U.S. PATENT DOCUMENTS

| | | | |
|---|---|---|---|
| 7,725,150 B2* | 5/2010 | Tupin, Jr. | A61B 5/05 382/128 |
| 8,562,526 B2 | 10/2013 | Heneghan et al. | |
| 8,692,717 B2 | 4/2014 | Friedman | |
| 8,721,559 B2* | 5/2014 | Peterson | A61B 5/02028 600/526 |
| 8,781,563 B2 | 7/2014 | Foo | |
| 9,492,099 B2* | 11/2016 | Gamble | A61B 5/0507 |
| 2002/0008655 A1* | 1/2002 | Haj-Yousef | G01V 3/12 342/22 |
| 2004/0249258 A1* | 12/2004 | Tupin, Jr. | A61B 5/05 600/407 |
| 2005/0043608 A1* | 2/2005 | Haj-Yousef | A61B 5/053 600/407 |
| 2008/0045832 A1* | 2/2008 | McGrath | A61B 5/024 600/427 |
| 2008/0077015 A1 | 3/2008 | Boric-Lubecke et al. | |
| 2008/0234574 A1* | 9/2008 | Hancock | A61B 5/0507 600/430 |
| 2010/0022900 A1* | 1/2010 | Peterson | A61B 5/02028 600/508 |
| 2013/0231550 A1 | 9/2013 | Weinstein et al. | |

FOREIGN PATENT DOCUMENTS

| | | |
|---|---|---|
| EP | 2700353 A1 | 2/2014 |
| WO | 2010132850 A1 | 11/2010 |

OTHER PUBLICATIONS

Katabi, "Tracking People and Monitoring Their Vital Signs Using Body Radio Reflections", Proceedings of the 2014 Workshop on Physical Analytics, 2014, p. 45, 1 page.

* cited by examiner

APPARATUS AND METHOD FOR ESTIMATING A VALUE OF A PHYSIOLOGICAL CHARACTERISTIC

TECHNICAL FIELD OF THE INVENTION

The invention relates to a measurement apparatus and method for estimating a value of a physiological characteristic of a subject, and in particular relates to a measurement apparatus and method for estimating one or more vital parameters of the subject using radio frequency (RF) radiation applied to the body of the subject.

BACKGROUND TO THE INVENTION

In many clinical scenarios where access to hospital monitoring equipment is not available (including, e.g., home care, emergency care both in and out of hospitals, and screening/triage in remote locations) it is desirable to be able to check a subject's vital parameters. For example, when an unconscious person is found the presence or absence of circulation and ventilation should be assessed as soon as possible. It would also be desirable to quickly check vital parameters of subjects in hospital waiting rooms in order to identify which subjects are most in need of rapid treatment. At present there is limited technology available which can perform this function, and many existing technologies are expensive, difficult to use, and/or unreliable.

Prior art systems based on time-of-flight (TOF) measurements of reflected radio waves exist which can determine global body parameters (i.e. position and posture). However; these are typically unable to measure physical parameters inside of the body. For example, the WiZ system proposed by researchers at MIT is a multi-person centimeter-scale motion tracking system that pinpoints people's locations using only detected RF reflections from their bodies. WiZ can further track a person's breathing and heartbeat remotely, without requiring any body contact, by detecting the minute movements associated with breathing and heartbeat (e.g., the chest movements caused by the inhale-exhale process). It operates by transmitting a low-power wireless signal and monitoring its reflections. Distances to a reflecting object are measured using the TOF of the signal (i.e. the time it takes the signal to travel from the transmitter to a reflector and back). This system requires multiple transmit antennas and multiple receive antennas. Furthermore, because only a small portion of the 3D space into which signals are transmitted is modulated by the volume-of-interest, it is difficult to achieve good SNR and signal-to-crosstalk. The receiver must therefore be highly sensitive and have low phase noise. Because of these requirements, systems like WiZ are not suitable for use in most scenarios which occur outside the clinic where it is desired to measure vital parameters.

A quick and reliable means of checking the vital parameters of a subject would be a valuable tool to improve outcomes in such scenarios. There is therefore a need for an improved method and apparatus that can quickly provide a reliable estimate of one or more physiological characteristics of a subject.

SUMMARY OF THE INVENTION

According to a first aspect of the invention, there is provided a measurement apparatus for estimating a value of a physiological characteristic of a subject. The measurement apparatus comprises a radio-frequency (RF) power generating apparatus, a detector, and a controller in communication with the RF power generating apparatus. The RF power generating apparatus comprises a transmit antenna for emitting RF radiation; an RF signal generator; and a transmission line connecting the RF signal generator to the transmit antenna. The detector is arranged to measure the variation of at least one parameter correlated with attenuation of the emitted RF radiation, during the measurement period. The controller is arranged to cause the RF power generating apparatus to emit RF radiation during a measurement period; receive measurements of the variation of the at least one parameter from the detector; and calculate a value of a physiological characteristic of a subject based on the received measurements.

Thus, embodiments of the claimed invention can estimate vital parameters of a subject by measuring the time-varying attenuation of local RF radiation applied to the body. This attenuation is modulated by fluid content modulations inside the body, mainly due to heartbeats, breathing, and arterial blood pulsations. Advantageously, embodiments of the invention can be implemented as a pocket-sized, stand-alone device, or can be integrated into existing devices which incorporate RF technology, such as smartphones and tablets.

In some embodiments of the invention the detector comprises at least one directional coupler connected to the transmission line. In some such embodiments the at least one parameter correlated with attenuation of the emitted RF radiation comprises a parameter related to the amount of RF power reflected by an interface between the transmit antenna and the transmission line. Additionally or alternatively, in such embodiments the at least one parameter correlated with attenuation of the emitted RF radiation comprises a level of power output by the transmit antenna. In some embodiments in which the at least one parameter correlated with attenuation of the emitted RF radiation comprises a level of power output by the transmit antenna, the impedance of the RF signal generator is matched to the impedance of the transmission line. Alternatively or additionally, in some such embodiments the free space impedance of the antenna is matched to the impedance of the transmission line.

In some embodiments the at least one parameter correlated with attenuation of the emitted RF power comprises one of: a level of DC power input to the RF signal generator; and a level of DC current input to the RF signal generator. In some such embodiments the detector is arranged to monitor the level of DC current supplied to the RF signal generator. In some such embodiments the impedance of the RF signal generator is matched to the impedance of the transmission line. Alternatively or additionally, in some such embodiments the free space impedance of the antenna is matched to the impedance of the transmission line.

In some embodiments the detector comprises a receive antenna connected to the controller by a further transmission line. In some such embodiments the at least one parameter correlated with attenuation of the emitted RF power comprises a level of RF power detected by the receive antenna.

In some embodiments the transmit antenna and the RF signal generator are provided within a single device housing. In some such embodiments the controller is also provided within the single device housing.

In some embodiments the apparatus comprises a smartphone.

In some embodiments the measurement apparatus comprises a measurement part configured to be attached to a subject, and a separate reader part configured to wirelessly communicate with the measurement part using RF radiation.

In some embodiments the RF power generating apparatus is configured to generate RF radiation having a frequency of one or more of: 2.4 GHz, 2.5 GHz, 5 GHz and 13.5 MHz.

There is also provided, according to a second aspect of the invention, a sensor part for embodiments of the measurement apparatus of the first aspect which comprises a measurement part configured to be attached to a subject, and a separate reader part configured to wirelessly communicate with the measurement part using RF radiation. The sensor part comprises the RF power generating apparatus, the detector and a first wireless communication apparatus. In an embodiment of the sensor part the first wireless communication apparatus comprises one of: near-field communications, NFC, apparatus and radio-frequency identification, RFID, apparatus.

There is also provided, according to a third aspect of the invention, a reader part for embodiments of the measurement apparatus of the first aspect which comprise a measurement part configured to be attached to a subject, and a separate reader part configured to wirelessly communicate with the measurement part using RF radiation. The reader part comprises the controller and a second wireless communication apparatus. In an embodiment of the reader part the second wireless communication apparatus comprises one of: near-field communications, NFC, apparatus and radio-frequency identification, RFID, apparatus.

There is also provided, according to a further aspect of the invention, a wearable measurement device which comprises a sensor attachable to a subject, a transmit antenna for emitting RF radiation, an RF signal generator, a transmission line connecting the RF signal generator to the transmit antenna, a detector arranged to measure a variation of at least one parameter correlated with an attenuation of the emitted RF radiation, during a measurement period, and a first wireless transceiver for sending the measured variation of the at least one parameter to a receiving end. The receiving end may for example be a patient monitor comprising a second wireless transceiver for receiving the measured variation of the at least one parameter. The patient monitor may initiate the measurement performed by the wearable measurement device and the measurement period may be programmable by a caregiver such that the wearable measurement device is measuring under control of the patient monitor. A microcontroller in the patient monitor has a program that causes the microcontroller in the patient monitor to communicate with the RF signal generator and the detector in the wearable measurement device such that the microcontroller causes the RF signal generator to emit RF radiation during the measurement period; the microcontroller receives measurements of the variation of the at least one parameter from the detector, and calculates a value of a physiological characteristic of a subject based on the received measurements. In dependence of a comparison of the calculated value of the physiological characteristic and a threshold the patient monitor may provide a visible and/or audible alarm. The physiological characteristic may be heart rate, respiration rate or fluid content of the subject. In an embodiment the wearable measurement device is included in a patch that is attached to the skin of the subject.

There is also provided, according to a fourth aspect of the invention, a method of estimating a value of a physiological characteristic of a subject. The method comprises:
  placing a transmit antenna adjacent to a body part of the subject;
  generating a radio-frequency, RF, signal and transmitting it to the transmit antenna via a transmission line during a measurement period,
  emitting, from the transmit antenna, in accordance with the generated RF signal, RF radiation into the body part of the subject during the measurement period;
  measuring the variation of at least one parameter correlated with attenuation of the emitted RF radiation during the measurement period; and
  calculating a value of a physiological characteristic of the subject based on the measured variation of the at least one parameter.

In some embodiments the physiological characteristic is one of: heart rate; respiration rate.

There is also provided, according to a fifth aspect of the invention, a computer program product, comprising computer readable code embodied therein. The computer readable code is configured such that, on execution by a suitable computer or processor, the computer or processor:
  causes an RF power generating apparatus to emit RF radiation during a measurement period;
  receives measurements of the variation of at least one parameter correlated with attenuation of the emitted RF radiation from a detector during the measurement period; and
  calculates a value of a physiological characteristic of a subject based on the received measurements.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE PREFERRED EMBODIMENTS

Figure 1:
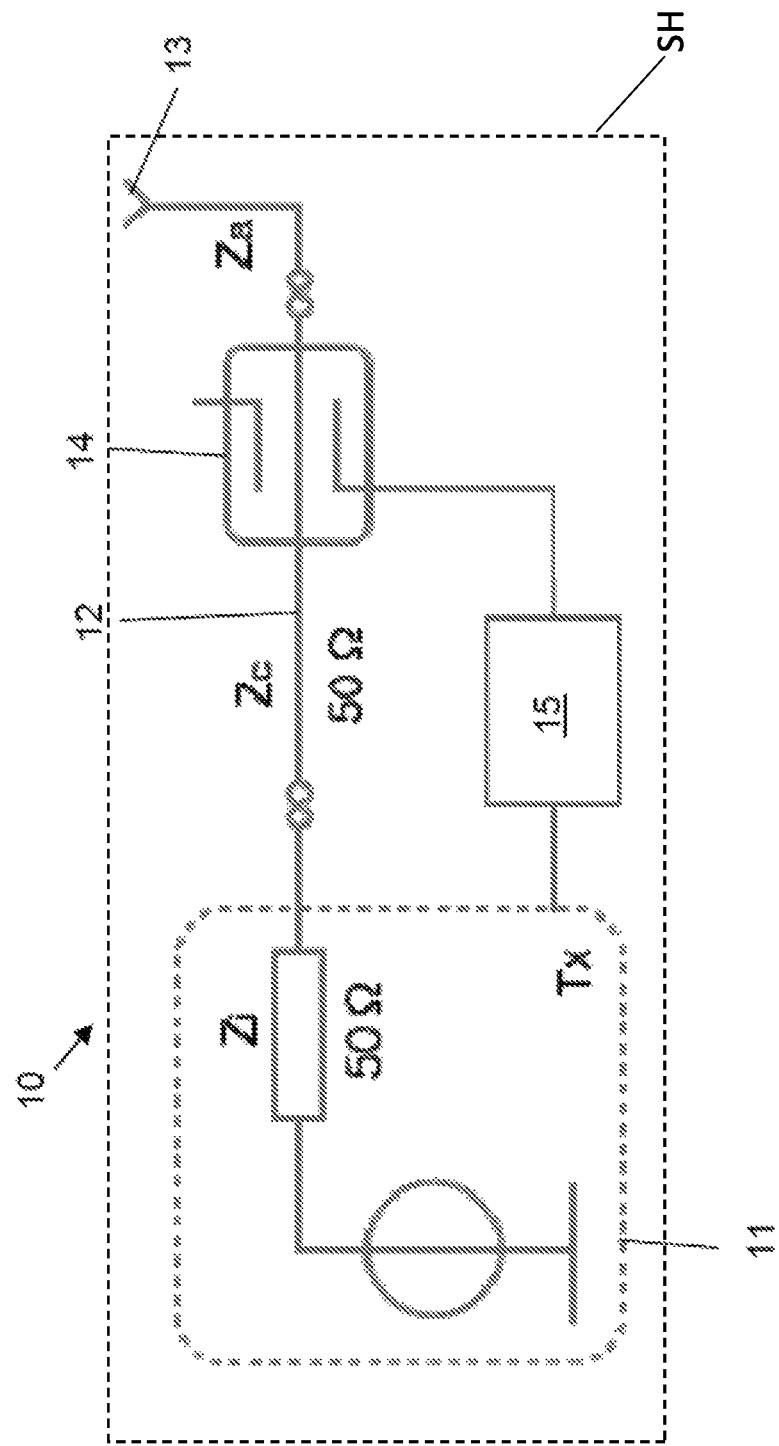
FIG. 1 is an illustration of an apparatus according to a first embodiment of the invention.

FIG. 1 shows a measurement apparatus for estimating one or more physiological characteristics of a subject (e.g. a patient or an elderly person) according to a first embodiment of the invention. In preferred embodiments the measurement apparatus is able to estimate one or more vital parameters of the subject. The measurement apparatus 10 comprises an RF generating apparatus, a detector in the form of a directional coupler 14, and a controller 15. The RF generating apparatus comprises a signal generator 11 which is connected via a transmission line 12 to an antenna 13. The directional coupler 14 is inserted in the transmission line 12. The controller 15 is in communication with the RF signal generator 11 and the directional coupler 14, such that the controller 15 can send control signals to the RF signal generator 11 and receive measurement data from the directional coupler 14.

In some embodiments the antenna 13 is a quarter wavelength WiFi antenna. Alternatively the antenna 13 can be a half wavelength dipole antenna or a folded dipole antenna. The antenna 13 can be a directional antenna (i.e. one which radiates greater power in one or more particular directions) or an omnidirectional antenna (i.e. one which radiates equal power in all directions). The transmission line can be of any suitable type known in the art. In some embodiments the transmission line is un-balanced (e.g. coaxial). In alternative embodiments the transmission line is balanced (e.g. twin-axial or twin-lead). In some embodiments the length of the transmission line is very small (or virtual zero). In some embodiments the signal generator is configured to apply a 2.4 GHz continuous wave signal. In some embodiments the antenna 13 is provided as a separate component to the signal generator 11 and is connected to the signal generator by a cable. In some such embodiments the transmission line 12 comprises a 50Ω coaxial cable. In alternative embodiments the antenna 13, signal generator 11, and directional coupler 14 are provided within a single device housing SH. In some embodiments the RF signal generator 11 and the transmission line 12 are impedance matched. In some embodiments the impedance of the antenna 13 in free space is matched to the impedance of the transmission line 12.

In use the antenna 13 is placed close to the body of the subject. It will be appreciated that how close the antenna needs to be depends on factors such as the type of the antenna and the frequency of the emitted RF radiation; however, it is expected that typically the antenna or a device housing the antenna will be held in contact with the subject's body, or with clothing worn by the subject. Galvanic contact is not required, nor is it necessary for the antenna to be in direct contact with the skin of the subject. A directional antenna will generally not need to be as close as an omni-directional antenna. Where on the subject's body the antenna is placed will depend on which physiological characteristic is being measured. If heart rate is being measured, preferably the antenna is placed close to an artery. If breathing rate is being measured, preferably the antenna 13 is placed adjacent the chest of the subject. However; in some cases it is also possible to measure breathing rate when the antenna 13 is placed adjacent the upper abdomen of the subject. It will be appreciated that in embodiments in which the antenna is integral with the other components of the measurement apparatus 10 in a single device housing, placing the antenna 13 close to the body of the subject comprises placing the measurement apparatus 10 close to the body of the subject.

When the antenna 13 has been placed in a suitable position for measurement, the controller 15 controls the RF signal generator 11 (e.g. by sending a control signal to the RF signal generator 11) to generate an RF signal and transmit it to the antenna 13 via the transmission line 12. The antenna 13 thereby emits RF radiation into the body of the subject in accordance with the generated RF signal. The controller controls the RF signal generator to generate the RF signal for a period of time (hereinafter referred to as the measurement period). In some embodiments the duration of the measurement period is predetermined In some embodiments the duration of the measurement period is 5-30 seconds. In some embodiments the duration of the measurement period is determined in dependence on the physiological characteristic being estimated. In some such embodiments the duration of the measurement period is defined such that it includes a minimum number of cycles of a physiological process, e.g. a minimum number of breaths or heartbeats. A longer measurement period can improve the accuracy of the estimated physiological characteristic value(s); however, it will be appreciated that increasing the duration of the measurement period reduces the speed and ease-of-use of the measurement apparatus.

In preferred embodiments the frequency of the emitted RF radiation falls within an Industrial-Scientific-Medical (ISM) band. In some such embodiments the RF radiation has a frequency of 2.4-2.5 GHz or 5 GHz (i.e. the frequencies used by WiFi systems and BlueTooth systems). Advantageously, electronic components for these frequencies are readily available and are incorporated into many existing portable electronic devices. In other such embodiments the RF radiation has a frequency of 13.5 MHz (i.e. the frequency used by Near Field Communication (NFC) systems). Advantageously, in such embodiments the waves penetrate deeper into the tissue. This could enable the detection of, e.g., the heartbeat of a fetus inside the womb. Furthermore, many existing smartphones are equipped with NFC systems.

Fluid in close proximity (typically 0.1-2 cm) to the antenna 13 attenuates the applied RF field and effectively changes the impedance of the antenna 13. When an electromagnetic wave traveling through an antenna system encounters differences in impedance, some fraction of the wave's power is reflected back to the source by the interface between the two different impedances, forming a standing wave in the transmission line 12. The amount of power reflected depends on the size of the mismatch between the impedances, and is therefore correlated with the degree of attenuation of the emitted RF radiation. It will be appreciated that in embodiments in which the impedances of RF generator 11, the transmission line 12 and the antenna 13 (in free field) are matched, no reflection will occur when the antenna is located in free space. Thus, when the antenna is in proximity to a subject's body or other fluid containing object, variations in the amount of fluid present in the volume-of-interest (i.e. the volume which receives RF radiation from the antenna 13) cause variations in the antenna impedance, which consequently changes the amplitude of the reflected wave and hence the power level of the reflection signal. The amplitude of the reflected wave will vary in dependence on the fluid changes regardless of whether the RF generator, transmission line and/or antenna (in free field) are impedance matched, therefore it will be appreciated that such impedance matching is not essential. Indeed, in embodiments in which the power of the reflected wave is measured (such as the embodiment shown in FIG. 1), it is advantageous for the (free field) impedance of the antenna 13 not to be matched to the impedance of the transmission line 12. This is because the measured power signal does not have a sign (i.e. + or −), so any impedance deviation (regardless of direction) causes an increase in the signal magnitude.

The reflected power is detected by the directional coupler 14, which measures the power level of the reflection signal. In other words: fluid movement in the volume-of-interest modulates the impedance mismatch between the antenna 13 and the transmission line 12, which in turn modulates the power level of the reflection signal measured by the directional coupler 14. (In embodiments where the length of the transmission line 12 is virtual zero, the reflection from the interface between the antenna 13 and the RF signal generator 11 is measured, rather than the reflection from the interface between the antenna 13 and the transmission line 12). The measured power level is sent by the directional coupler 14 to the controller 15 for processing.

Both heartbeat and respiration cause fluid to move in the volume-of-interest. A subject's heartbeat causes the volume of blood in a given section of artery to vary cyclically in time with their heart rate (HR). Meanwhile, respiration causes the subject's lungs to cyclically expand and collapse. When the lungs are expanded a volume-of-interest which includes at least part of the lungs contains a greater volume of air (and thus a lower volume of fluid) than when the lungs are collapsed. Depending on the placement of the antenna 13, one or both of HR and respiration rate will therefore contribute to the modulation of the reflected power measured by the directional coupler 14. The transmitted signal power, the standing wave ratio (VSWR or SWR) (i.e. the ratio of maximum power to minimum power in the standing wave formed by the reflected power), the reflection coefficient (of the interface between the transmission line 12 and the antenna 13), and the complex amplitude ratio of reflected versus initial waves will also vary in dependence on changes in the fluid content of the volume-of-interest, and are therefore also correlated with the degree of attenuation of the emitted RF radiation caused by fluid.

In some embodiments one or more of these parameters are measured or determined alternatively or additionally to the reflected signal power, using any suitable techniques known in the art. For example, the transmitted signal power can be measured by inserting a directional coupler into the transmission line 12 which is arranged to detect forward power, rather than reflected power. In embodiments in which a directional coupler is used to measure transmitted signal power, preferably the impedances of at least the RF signal generator and the transmission line are matched. This advantageously causes the reflected wave to be fully absorbed in the signal generator instead of reflecting back to the antenna. Combining measurements of a plurality of RF parameters can advantageously provide more detailed information about the variations in RF absorption caused by changing fluid content.

If the antenna 13 is well calibrated and its location (i.e. in relation to the body of the subject) is well-defined, the absolute fluid content can be determined using one or more of the measured RF parameters listed above. However; placing stringent requirements on the calibration and placement of the antenna 13 would significantly complicate the operation of the measurement apparatus 10, making it less suitable for use in home care or emergency scenarios. Therefore, in preferred embodiments an absolute fluid content value is not determined Instead, in such embodiments the controller 15 calculates a value of one or more physiological characteristics based only on the time variance of the measured parameter(s) (i.e. the variation of the measured parameter(s) during the measurement period).

Figure 2A:
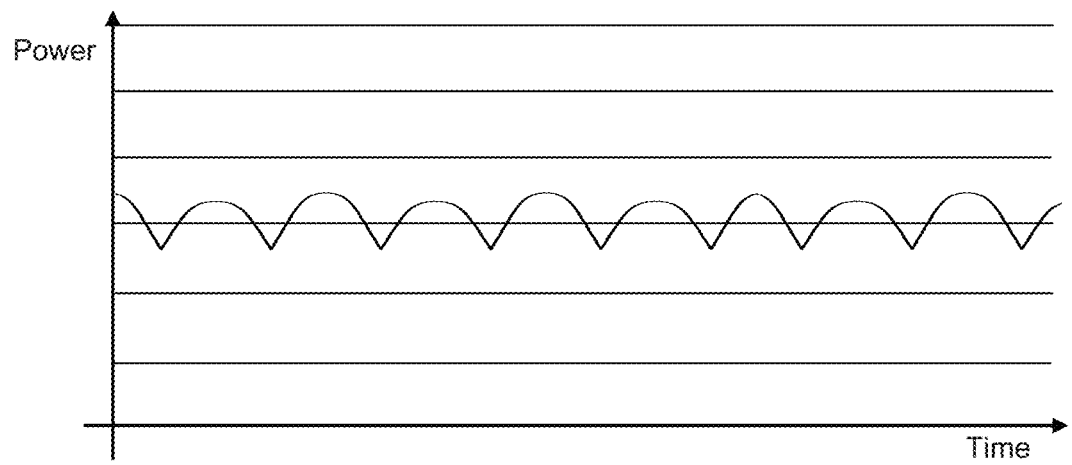
FIG. 2a shows a first example of a signal measured by the apparatus of FIG. 1.
Figure 2B:
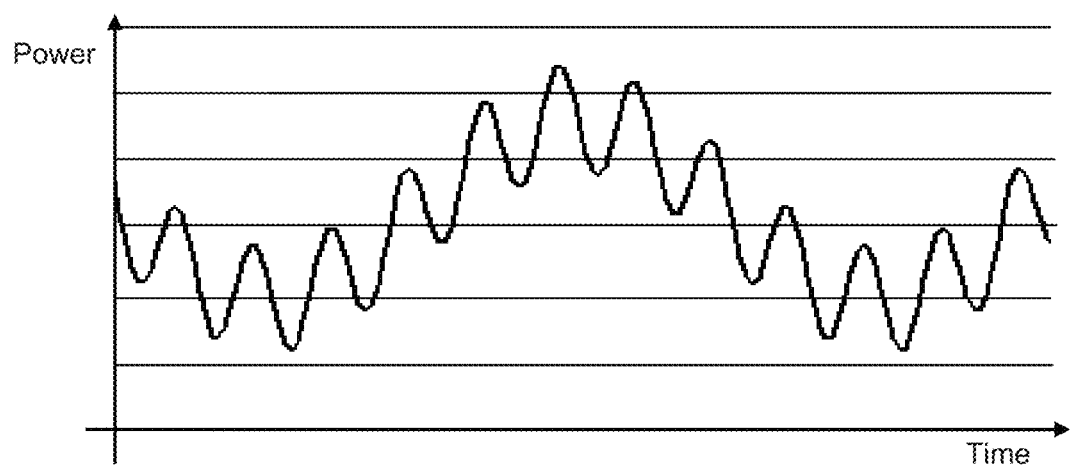
FIG. 2b shows a second example of a signal measured by the apparatus of FIG. 1.

In the FIG. 1 embodiment, the signal output by the directional coupler 14 is demodulated by a spectrum analyzer (which is comprised in the controller 15). FIGS. 2a and 2b show example waveforms for the measured reflected power produced by the spectrum analyzer corresponding to the cases where only blood movement is detected (FIG. 2a) (this would occur, for example, if the antenna 13 was placed adjacent the subject's wrist) and where both blood movement and lung movement are detected (FIG. 2b). It can clearly be seen from FIG. 2b that the variations caused by blood movement occur over a significantly shorter timescale than the variations caused by lung movement. Numerical values for HR and/or respiration rate are extracted from the waveform generated by the spectrum analyzer using suitable post-processing techniques (e.g. time-domain filtering, FFT, correlation techniques). The accuracy of the physiological characteristic values output by the measurement apparatus 10 increases with the number of cycles (i.e. breaths or heartbeats) included in the analyzed signal. A minimum of two cycles should be included in the analyzed signal in order to produce a reliable result. Preferably 5-10 cycles are included in the analyzed signal.

Figure 3:
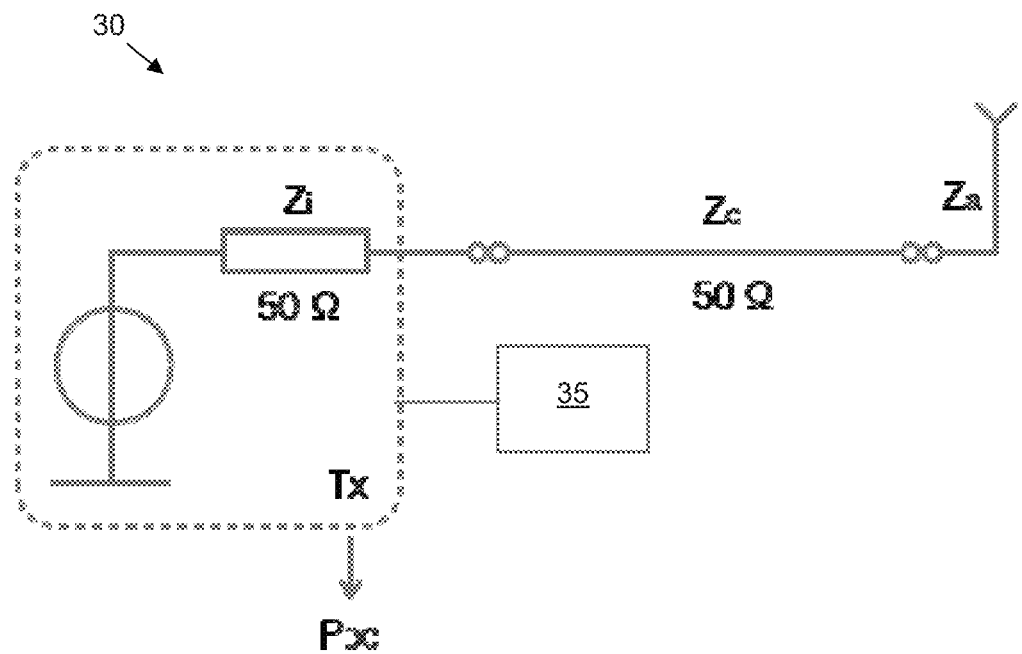
FIG. 3 is an illustration of an apparatus according to a second embodiment of the invention.

FIG. 3 shows a second embodiment of the invention. Unlike in the first embodiment, the detector used by the measurement apparatus 30 of the second embodiment is not a directional coupler, and consequently the controller 35 is in communication only with the RF signal generator. All of the other components are the same as in the first embodiment. Because no directional coupler is available, it is not possible to directly measure the reflected power resulting from the varying impedance mismatch between the antenna and the transmission line. Instead one or more of the level of the DC power or the DC current input to the RF signal generator can be used as proxy for the amount of reflected power. The detector in this embodiment therefore comprises any suitable circuitry known in the art for measuring DC input power or DC input current to the RF generating apparatus (such circuitry will typically be provided as part of the controller). Preferably in embodiments in which DC input power or DC input current is measured, the impedances of at least the RF signal generator and the transmission line are matched so that multiple reflections (i.e. from an interface between the RF signal generator and the transmission line as well as from the interface between the antenna and the transmission line) are avoided.

The RF generating apparatus (i.e. the signal generator plus transmission line plus antenna) is tuned to achieve a maximum power output for a minimum power input (which is obtained when the impedances of the RF signal generator and the antenna both match that of the transmission line). When an impedance mismatch occurs (e.g. as a result of a change in the fluid content of the volume-of interest), some of the input current (and hence some of the input power) is reflected by the interface, as explained above. This causes the RF power output by the antenna to drop. In some embodiments the measurement apparatus 30 is configured to maintain a given level of output power. To achieve this, the RF signal generator must draw more input power (and therefore more current) as the mismatch increases to offset the power being reflected by the interface. The level of the DC power and the DC current input to the RF signal generator therefore varies together with the effective impedance of the transmission line, which in turn varies with the amount of fluid in the volume-of-interest. Either of the DC input power or DC input current can therefore be measured to produce a time varying signal which is modulated by changes in the fluid distribution in the volume-of-interest.

The DC power or current input signal (and the RF power output signal) is less clean than the reflected power signal output by a directional coupler, and therefore the controller 35 must perform more processing to extract physiological characteristic values than the controller 15 of the first embodiment. In particular the relationship between antenna impedance and DC current must be determined during a calibration stage of the measurement apparatus. This relationship depends on, among other factors, the length of the transmission line (i.e. how many wavelengths).

This embodiment is advantageous because it can be implemented by RF circuitry which is already present in many common portable electronic devices. For example, the WiFi circuitry of a smartphone or tablet comprises an RF signal generator coupled to an antenna via a transmission line, as well as the means to measure at least one of the internal RF output power and the DC input power of the RF generating apparatus (either of which can be used a proxy for antenna-transmission line impedance mismatch, as explained above). Alternatively, the Near Field Communications (NFC) hardware present in many smartphones can be used. NFC communication depends on modulation, by, e.g., a wireless tag, of an RF field emitted by an NFC reader. This modulation is measured by the NFC reader. NFC hardware can therefore be used to measure RF modulation caused by fluid volume changes in the body, as required by embodiments of the invention. Suitable control software can easily be provided to the smartphone, for example in the form of an app.

Smartphones are widespread, making them particularly suitable for use in emergency care and home care environments. A further advantage is that smartphones typically incorporate other types of sensors, such as accelerometers, cameras and microphones. Data recorded by one or more of these other sensors simultaneously with obtaining the RF signal can be correlated with the RF signal to enhance the accuracy of the output physiological characteristic values. For example, in some embodiments a camera is used to record a video of the subject's chest during the RF measurement period. The recorded image data is then analyzed to detect chest movements resulting from the subject's breathing, which can be used to generate an independent estimate of the respiration rate. This can then be combined with the estimate generated from the RF signal to improve the accuracy of the final calculated value. In some embodiments a microphone is used to record the subject's breathing sounds during the RF measurement period, and this data is combined with the RF data in a similar manner to that described in relation to the camera data. In some embodiments in which the measurement apparatus is configured to be held against the subjects chest during the RF measurement period (i.e. embodiments in which the antenna is within the main device housing), the measurement apparatus includes an accelerometer. The accelerometer detects movement of the measurement apparatus caused by the expansion and contraction of the subject's lungs and chest during the RF measurement period. The accelerometer data is combined with the RF data in a similar manner to that described in relation to the camera data.

Data from any additional sensors can also advantageously be used to detect and remove artifacts from the RF signal. For example, accidental movement of the antenna in relation to the subject will likely cause a change in the volume of fluid in the volume-of-interest, but this change will have no relation to the physiological characteristic being estimated. An accelerometer located in the same housing as the antenna would detect this movement, and allow the resulting effect on the RF signal to be identified and corrected. Camera and/or microphone data could similarly be used to detect unintended movements of a measurement apparatus during the RF measurement period.

Figure 4:
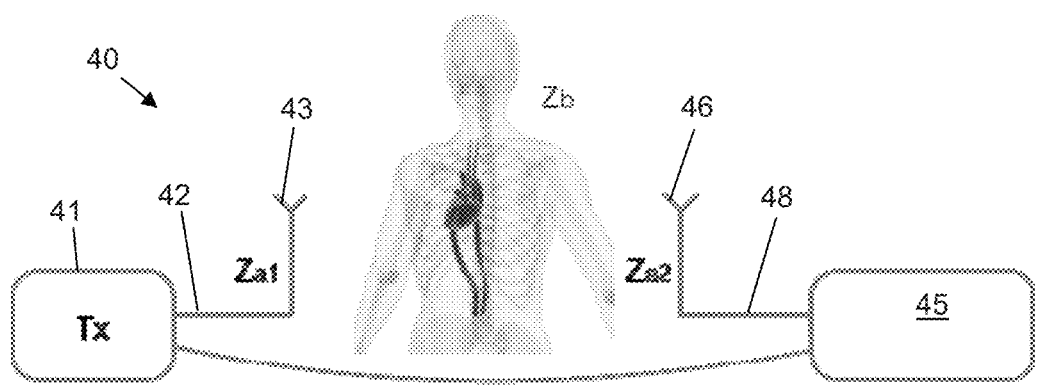
FIG. 4 is an illustration of an apparatus according to a third embodiment of the invention.

FIG. 4 shows a measurement apparatus 40 according to a third embodiment of the invention. The measurement apparatus 40 comprises RF generating apparatus in the form of an RF signal generator 41 which is connected via a first transmission line 42 to a first (transmit) antenna 43. A controller 45 is provided in communication with the RF signal generator 41. The measurement apparatus 40 further comprises a second (receive) antenna 46, which is connected via a second transmission line 48 to network analyzer in the controller 45. In some embodiments the second antenna 46 is of the same type as the first antenna 43. Alternatively, the second antenna 46 is a directional antenna which can be used at a larger distance from the subject, such that most or all of the body of the subject is within the field of view of the second antenna 46. In such alternative embodiments the second antenna 46 can be used to acquire information from different regions of the body.

In use, the first antenna 43 is arranged adjacent to a first side of a body part of a subject and the second antenna 46 is arranged adjacent to an opposite side of a body part of the subject, such that the second antenna 46 detects the RF radiation emitted by the first antenna 43 after it has passed through the body part of the subject. The received signal is therefore affected by the RF damping due to the fluid volume in the pathway between the first and second antennas. The received signal is also affected by the impedance mismatch between the first antenna 43 and the first transmission line 42 and by the impedance mismatch between the second antenna 46 and the second transmission line 48.

The (complex) RF transfer function of the pathway between the first and second antennas is determined by comparing the transmitted signal generated by the RF signal generator 41 to the signal received by the second antenna 46 (e.g. using the network analyzer in the controller 45). This transfer function varies in dependence on the fluid volume in the pathway, and will therefore contain information relating to the subject's HR and/or breathing rate (depending on the placement of the antennas 43, 46). The controller 45 generates estimated values for one or more physiological characteristics based on the time-varying transfer function, using any suitable signal processing techniques known in the art. For example, proper characterization and/or calibration is needed for each antenna-cable combination to relate the measured RF transfer function to the actual fluid volume in the pathway.

Monitoring devices according to this embodiment of the invention can advantageously produce more accurate estimates of a subject's vital parameters, because the first and second antennas can be placed such that the pathway between them includes the whole upper body of the subject. This maximizes the magnitude of the changes in fluid volume in the volume-of-interest which occur as a result of heartbeat or respiration, thus improving the signal to noise ratio of the measured signal.

Optionally, the impedance mismatch between the first antenna 43 and the transmission line 42 is also measured (e.g. by means of a directional coupler, in the manner of the first embodiment, or by measuring DC input power/current, in the manner of the second embodiment). Combining an estimated value of a physiological characteristic based on antenna mismatch with the estimated value based on the transfer function can advantageously improve the accuracy of the overall output physiological characteristic value.

In some embodiments (not illustrated), the measurement apparatus 40 further includes one or more additional transmit antennas and/or one or more additional receive antennas. This has the effect of improving the accuracy of the output physiological characteristic value(s).

Figure 5:
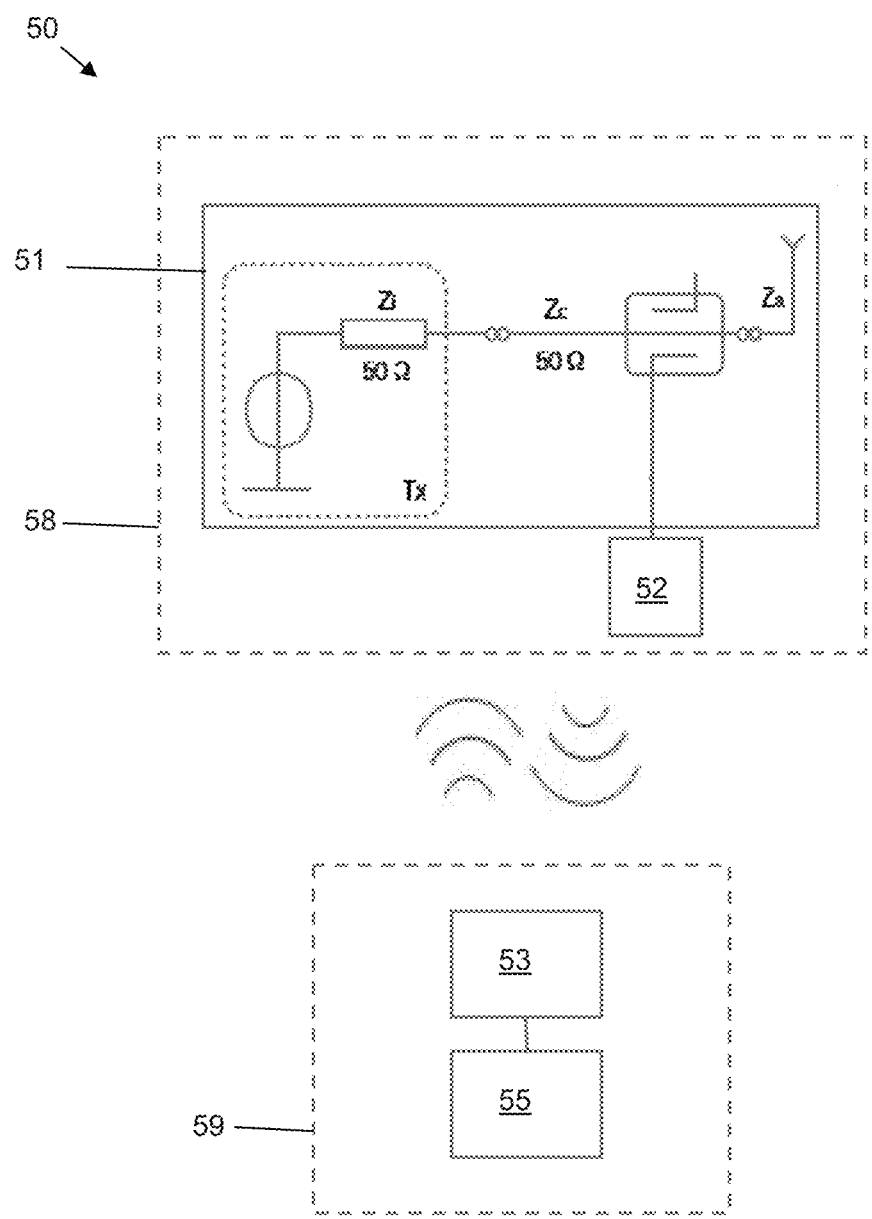
FIG. 5 is an illustration of an apparatus according to a fourth embodiment of the invention.

FIG. 5 shows a measurement apparatus 50 according to a fourth embodiment of the invention. The measurement apparatus 50 comprises a plaster 58 and a reader 59. A sensor apparatus 51 for detecting fluid volume changes in a volume-of-interest by means of emitting RF radiation into the volume-of-interest is integrated into the plaster 58, together with a first NFC apparatus 52. In the illustrated embodiment the sensor apparatus 51 operates in the same manner as the measurement apparatus 10 described above in relation to the first embodiment. Other embodiments are envisaged, however, in which the sensor apparatus 51 operates in the same manner as the measurement apparatus 30 described above in relation to the second embodiment. The plaster 58 is configured to be attached to the skin of a subject. The reader 59 comprises a control unit 55 in communication with a second NFC apparatus 53. In preferred embodiments the reader 59 is in the form of a portable handheld device. In some embodiments the reader 59 comprises a smartphone.

In use, the plaster is attached to the skin of the subject at a suitable position for detecting fluid movement related to the physiological characteristic of interest (e.g. blood flow in an artery, or lung fluid displacement due to respiration). To generate an estimated value for the physiological characteristic of interest, the reader 59 is placed near the plaster 58 and the second NFC apparatus 53 is activated (e.g. by a control signal from the controller 55). This causes the second NFC apparatus 53 to emit RF radiation having a frequency of 13.5 MHz, which is received by the first NFC apparatus 52 in the plaster. The RF circuitry in the plaster 58 becomes powered by the received RF radiation and performs a measurement in the manner described above in relation to the first embodiment (i.e. using a directional coupler to detect reflected power). The output signal from the directional coupler (hereinafter referred to as the measured signal) is sent to the first NFC apparatus 52, which transmits it to the reader 59. The second NFC apparatus 53 in the reader 59 receives the measured signal and sends it to the controller 55. The controller 55 processes the measured signal to generate an estimated value for one or more physiological characteristics, in the manner described above in relation to the first embodiment.

In some alternative embodiments RFID technology is used instead of NFC technology to enable communication between the RF circuitry within the plaster and the reader. In such embodiments the frequency of the RF radiation used to activate the RF circuitry within the plaster is 2.45 GHz.

This approach is advantageous because the location of the plaster, and therefore the sensor apparatus, is fixed in relation to the subject's body. This reduces or eliminates unintentional movement of the sensor apparatus during the RF measurement period, and consequently improves the accuracy of the output physiological characteristic value(s). Furthermore, the plaster can be left attached to the subject between measurements, which decreases measurement-to-measurement variations. It is also advantageous in facilitating the monitoring of physiological characteristics which relate to a slow change in fluid volume in the volume of interest. For example fluid changes in tissue caused by dehydration or pulmonary edema typically occur over several hours or days. Fixing the location of the sensor apparatus for a period of several days permits such slow changes to be detected. These features are especially advantageous for monitoring applications. For example, a measurement apparatus according to the fourth embodiment of the invention would be especially suitable for monitoring fluid changes in hospitalized patients, and/or for monitoring for the onset of pulmonary edema in home-based heart failure patients.

There is therefore provided a measurement apparatus that allows one or more vital parameters (or other physiological characteristics) of a subject to be estimated quickly and reliably. The measurement apparatus can be implemented as a small, easy-to-use, portable device. The measurement apparatus can advantageously used as a spot-checking tool in emergency situations, and/or to facilitate regular monitoring, e.g. in home care situations.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A measurement apparatus, comprising:
a transmit antenna for emitting radio frequency (RF) radiation, wherein the transmit antenna is placed in proximity to a body part of a subject such that a variation in an amount of fluid present in the body part of the subject causes a variation in an impedance of the transmit antenna;
an RF signal generator;
a transmission line connecting the RF signal generator to the transmit antenna;
a detector configured to measure a variation of a parameter correlated with the variation in the impedance of the transmit antenna during a measurement period; and
a controller, in communication with the RF signal generator and the detector, and configured to:
cause the RF signal generator to provide an RF signal to the transmit antenna such that the transmit antenna emits the RF radiation during the measurement period;
receive measurements of the variation of the parameter during the measurement period from the detector; and
calculate a value of a physiological characteristic of the subject based on the measurements,
wherein the parameter correlated with the variation in the impedance of the transmit antenna is a level of RF power reflected by an interface between the transmit antenna and the transmission line.

2. The measurement apparatus of claim 1, wherein the detector comprises at least one directional coupler connected to the transmission line.

3. The measurement apparatus of claim 1, wherein the measurement apparatus comprises a smartphone.

4. The measurement apparatus of claim 1, further comprising:
a sensor part configured to be attached to the subject; and
a separate reader part configured to wirelessly communicate with the sensor part using the RF radiation.

5. The measurement apparatus of claim 1, wherein the RF signal generator is configured to generate the RF radiation having a frequency of one or more of: 2.4 GHz, 2.5 GHz, 5 GHz, and 13.5 MHz.

6. The measurement apparatus of claim 4, wherein the sensor part comprises:
the RF power generating apparatus, the detector, and a first wireless communication apparatus.

7. The measurement apparatus of claim 6, wherein the first wireless communication apparatus comprises a near-field communications (NFC) apparatus or a radio-frequency identification (RFID) apparatus.

8. The measurement apparatus of claim 4, wherein the separate reader part comprises the controller and a second wireless communication apparatus.

9. The measurement apparatus of claim 8, wherein the second wireless communication apparatus comprises a near-field communications (NFC) apparatus or a radio-frequency identification (RFID) apparatus.

10. A method, comprising:
placing a transmit antenna in proximity to a body part of a subject such that a variation in an amount of fluid present in the body part causes a variation in an impedance of the transmit antenna, wherein the variation in the impedance of the transmit antenna is used to measure a physiological characteristic of the subject;
causing a radio-frequency (RF) signal to be generated with an RF signal generator, wherein the RF signal is transmitted to the transmit antenna via a transmission line during a measurement period;
causing RF radiation to be emitted into the body part of the subject via the transmit antenna during the measurement period;
receiving measurements of a variation of a parameter correlated with the variation in the impedance of the transmit antenna during the measurement period; and
calculating a value of the physiological characteristic of the subject based on the measurements,
wherein the parameter correlated with the variation in the impedance of the transmit antenna is a level of RF power reflected by an interface between the transmit antenna and the transmission line.

11. A tangible, non-transitory, computer readable medium storing computer readable code that, when executed by one or more processors of a computer, effectuate operations to measure a physiological characteristic of a subject, wherein a transmit antenna is placed in proximity to a body part of the subject such that a variation in an amount of fluid present in the body part causes a variation in an impedance of the transmit antenna, the operations comprising:
causing a radio-frequency (RF) signal to be generated with an RF signal generator, wherein:
the RF signal is transmitted to the transmit antenna via a transmission line during a measurement period, and
the transmit antenna is configured, based on the RF signal, to emit RF radiation into the body part during the measurement period;
receiving measurements of a variation of a parameter correlated with the variation in the impedance of the transmit antenna during the measurement period; and
calculating a value of the physiological characteristic of the subject based on the measurements,
wherein the parameter correlated with the variation in the impedance of the transmit antenna is a level of RF power reflected by an interface between the transmit antenna and the transmission line.

12. The measurement apparatus of claim 1, wherein the transmit antenna is placed in contact with the body part of the subject, the RF radiation emitted into the body part is attenuated by fluid in the body part and causes the impedance of the transmit antenna to change based on the amount of the fluid present in the body part.

13. The measurement apparatus of claim 1, further comprising:
a housing, wherein the transmit antenna, the RF signal generator, the detector, and the controller are within the housing, and wherein the detector comprises a directional coupler.

14. The measurement apparatus of claim 1, wherein the controller is further arranged to:
calculate an additional value of an additional physiological characteristic of the subject based on the measurements.

15. The measurement apparatus of claim 1, wherein the measurement period is determined based on the physiological characteristic to be measured.

16. The measurement apparatus of claim 1, wherein fluid movement in the body part causes a mismatch in an impedance of the transmission line and the impedance of the transmit antenna, and the variation of the parameter correlated with the variation in the impedance of the transmit antenna is modulated based on a size of a mismatch between the impedance of the transmission line and the impedance of the transmit antenna.

17. The measurement apparatus of claim 1, wherein the length of the transmission line is virtually zero, and the parameter correlated with the variation in the impedance of the transmit antenna is only one of:
a level of RF power reflected by an interface between the transmit antenna and the RF signal generator, or
the level of power output by the transmit antenna.

18. The method of claim 10, wherein the length of the transmission line is virtually zero, the parameter correlated with the variation in the impedance of the transmit antenna is only one of:
a level of RF power reflected by an interface between the transmit antenna and the RF signal generator, or
the level of power output by the transmit antenna.

19. The tangible, non-transitory, computer readable medium of claim 11, wherein the length of the transmission line is virtually zero, the parameter correlated with the variation in the impedance of the transmit antenna is only one of:
a level of RF power reflected by an interface between the transmit antenna and the RF signal generator, or
the level of power output by the transmit antenna.

* * * * *